(12) United States Patent
Dutzmann et al.

(10) Patent No.: US 6,423,726 B2
(45) Date of Patent: Jul. 23, 2002

(54) PESTICIDE

(75) Inventors: Stefan Dutzmann, Hilden; Christoph Erdelen, Leichlingen; Wolfram Andersch, Bergisch Gladbach; Heinz-Wilhelm Dehne, Bonn; Jürgen Hartwig, Leichlingen; Klaus Stenzel, Düsseldorf; Wolfgang Krämer, Burscheid, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/911,263

(22) Filed: Jul. 23, 2001

Related U.S. Application Data

(62) Division of application No. 09/585,227, filed on Jun. 1, 2000, now Pat. No. 6,297,263, which is a division of application No. 08/765,819, filed on Jan. 17, 1997, now Pat. No. 6,114,362.

(30) Foreign Application Priority Data

Jul. 28, 1994 (DE) ............................. 44 26 753

(51) Int. Cl.$^7$ ..................... A01N 43/40; A01N 47/10
(52) U.S. Cl. .................. 514/341; 514/478; 514/479
(58) Field of Search ................... 514/341, 478, 514/479

(56) References Cited

FOREIGN PATENT DOCUMENTS

| AU | A-21390/83 | 5/1984 |
| AU | A-29789/92 | 6/1993 |
| EP | 112284 | 6/1984 |
| EP | 545834 | 6/1993 |

OTHER PUBLICATIONS

English Abstract Only of DD 140,412 A (May 7, 1986) Lehmann H.
English Abstract Only of 88–129519/19 (Agricultural Chemistry) Nihon Tokushu Moyaku Sei (1998).
English Abstract Only of 88–129520/19 (Agricultural Chemistry) Nihon Tokushu Moyaku Sei (1998).

*Primary Examiner*—Allen J. Robinson
(74) *Attorney, Agent, or Firm*—Joseph C. Gil; John E. Mrozinski, Jr.

(57) ABSTRACT

A composition includes synergistic amounts of:
(a) a compound formula (I)

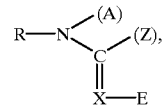

wherein X represents =CH— or =N—; E represents an electron-withdrawing radical; R represents optionally substituted hetarylalkyl; A represents hydrogen, alkyl, or a bifunctional group which is linked to the radical Z; Z represents alkyl, —NH-alkyl, —N(alkyl)$_2$ or a bifunctional group which is linked to the radical A, and (b) a fungicidal active compound, excluding cyclopropylcarboxamide derivatives and azolylmethylcycloalkanes. The combination of imidacloprid and a fungicidal active compound selected from the group consisting of tebuconazole and compounds of the formula

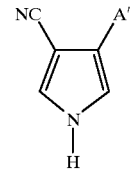

wherein A' represents

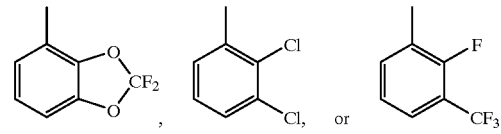

is excluded.

8 Claims, No Drawings

PESTICIDE

This is a Divisional application of Ser. No. 09/585,227, filed Jun. 1, 2000, issued as U.S. Pat. No. 6,297,263, which is a Divisional application of Ser. No. 08/765,819, filed Jan. 17, 1997, and issued as U.S. Pat. 6,114,362.

The present invention relates to pest control compositions which contain an active compound combination of certain agonists or antagonists of the nicotinic acetylcholine receptors of insects together with fungicides, their preparation and their use for the control of plant pests.

Agonists or antagonists of the nicotinic acetylcholine receptors of insects are known, for example from the following publications:

European Published Specifications No. 464 830, 428 941, 425 978, 386 565, 383 091, 375 907, 364 844, 315 826, 259 738, 254 859, 235 725, 212 600, 192 060, 163 855, 154 178, 136 636, 303 570, 302 833, 306 696, 189 972, 455 000, 135 956, 471 372, 302 389; German Published Specifications No. 3 639 877, 3 712 307; Japanese Published Specifications No. 03 220 176, 02 207 083, 63 307 857, 63 287 764, 03 246 283, 04 9371, 03 279 359, 03 255 072; U.S. Pat. Nos. 5,034,524, 4,948,798, 4,918,798, 4,918,086, 5,039, 686, 5,034,404; PCT Applications No. WO 91/17659, 91/4965; French Application No. 2 611 114; Brazilian Application No. 88 03 621.

The methods, processes, formulae and definitions described in these publications, and also the specific preparations and compounds described therein, are expressly referred incorporated herein.

Fungicidal active compounds, such as azole derivatives, aryl benzyl ethers, benzamides, morpholine compounds and other heterocycles are known (cf. K. H. Büchel "Pflanzenschutz und Schädlingsbekämpfung [Crop protection and pest control]", pages 140 to 153, Georg Thieme-Verlag, Stuttgart 1977, EP-OS (European Published Specification) 0 040 345, DE-OS (German Published Specification) 3 324 010, DE-OS (German Published Specification) 2 201 063, EP-OS (European Published Specification) 0 112 284, EP-OS (European Published Specification) 0 304 758, and DD-PS (German Democratic Republic Patent Specification) 140 412).

Mixtures of certain nitromethylene derivatives with fungicidal active compounds and their use as compositions for the control of pests in crop protection are already known (U.S. Pat. No. 4,731,385; JP-OS (Japanese Published Specifications) 63-68507, 63/68505, 63/72 608, 63/72 609, 63/72 610). Mixtures of certain open-chain nitromethylenes and nitroguanidines with fungicides are already known (JP-OS (Japanese Published Specification) 30 47 106; U.S. Pat. No. 5,181,587).

Mixtures of cyclopropylcarboxamides with certain nitromethylenene or nitroguanidine derivatives are already known (JP-OS (Japanese Published Specification) 3 271 207;

Mixtures of inter alia imidacloprid- and fungicidal active compounds for use in material protection and against termites, but not for use against plant-damaging pests, are already known (EP-OS (European Published Specification) (Nit 259)). Mixtures of imidacloprid and azolylmethylcycloalkanes, in particular triticonazole, are known from EP-OS (European Published Specification) 545 834.

However, nothing is yet known about nitroguanidine derivatives and fungicides other than cyclopropylcarboxamides and triticonazole influencing each other so favourably in over action that, while being well tolerated by plants, they can be used with outstanding effect as compositions for the control of plant pests.

The present invention relates to plant pest control compositions which contain compounds of the the general formula (I)

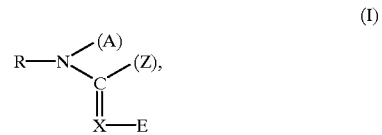

in which
X represents —CH= or =N—,
E represents an electron-withdrawing radical, in particular nitro or cyano,
R represents optionally substituted hetarylalkyl,
A represents hydrogen, alkyl, or a bifunctional group which is linked to the radical Z,
Z represents alkyl, —NH, alkyl, —N(alkyl)$_2$ or a bifunctional group which is linked to the radical A,
in mixtures with fungicidal active compounds, excluding cyclopropylcarboxamide derivatives and azolylmethylcycloalkanes.

Preferably, the invention relates to plant pest control compositions which contain compounds of the formula (I) in which the radicals have the following meaning:
X represents =CH— or =N—,
E represents $NO_2$ or CN,
R represents hetarylmethyl, hetarylethyl having up to 6 ring atoms and N, O, S, in particular N, as heteroatoms.

In particular there may be mentioned thienyl, furyl, thiazolyl, imidazolyl, pyridyl, which are optionally substituted.

Preferred examples of substituents are:
alkyl having preferably 1 to 4, in particular 1 or 2 carbon atoms, such as methyl, ethyl, n- and i-propyl and n-, i- and t-butyl; alkoxy having preferably 1 to 4, in particular 1 or 2 carbon atoms, such as methoxy, ethoxy, n- and i-propyloxy and n-, i- and t-butyloxy; alkylthio having preferably 1 to 4, in particular 1 or 2 carbon atoms, such as methylthio, ethylthio, n- and i-propylthio and n-, i- and t-butylthio; haloalkyl having preferably 1 to 4, in particular 1 or 2 carbon atoms and preferably 1 to 5, in particular 1 to 3 halogen atoms, wherein the halogen atoms are identical or different and wherein the halogen atoms are preferably fluorine, chlorine or bromine, in particular fluorine, such as trifluoromethyl; hydroxyl; halogen, preferably fluorine, chlorine, bromine and iodine, in particular fluorine, chlorine and bromine; cyano; nitro; amino; monoalkyl- and dialkylamino having preferably 1 to 4, in particular 1 or 2 carbon atoms per alkyl group, such as methylamino, methylethylamino, n- and i-propylamino and methyl-n-butylamino;
A represents hydrogen, $C_{1-4}$alkyl, in particular methyl or ethyl,
Z represents $C_{1-4}$alkyl, in particular ethyl or methyl, —NH($C_{1-4}$alkyl), —N($C_{1-4}$alkyl) or
A and Z, form together with the atoms to which they are bonded, form a saturated or unsaturated heterocyclic ring. The heterocyclic ring may contain a further 1 or 2 identical or different heteroatoms and/or heterogroups. Preferably, heteroatoms are oxygen or nitrogen and heterogroups are N-alkyl, the alkyl of the N-alkyl group containing preferably 1 to 4, in particular 1 or 2 carbon atoms. Examples of alkyl include methyl, ethyl, n-and i-propyl and n-, i-and t-butyl. The heterocyclic ring contains 5 to 7, preferably 5 or 6 ring members.

Examples of the heterocyclic ring include pyrrolidine, piperidine, thiazolidine, piperazine, imidazolidine, hexamethyleneimine, hexahydro-1,3,5-triazine, morpholine, which may optionally be substituted, preferably by methyl.

Most preferred are compounds of the general formulae (I) and (Ib)

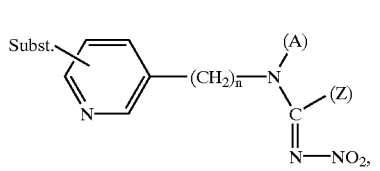
(Ia)

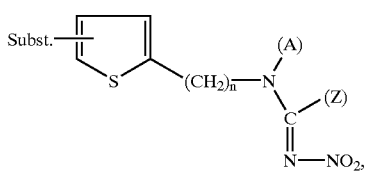
(Ib)

in which n represents 1 or 2,

Subst. represents one of the abovementioned substituents, in particular halogen, especially chlorine, A and Z have the abovementioned preferred meanings, Specifically, the following compounds may be mentioned:

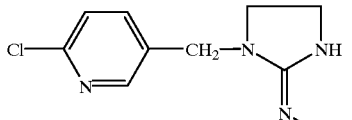

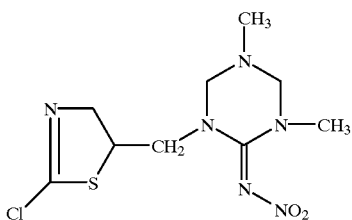

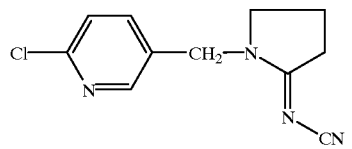

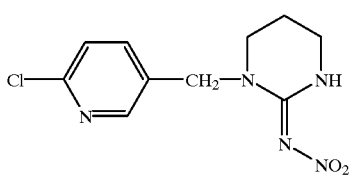

-continued

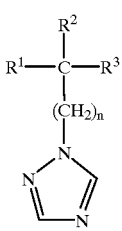

Fungicides in the novel compositions for the control of plant pests are for example:

(1) Azole derivatives of the formula (II)

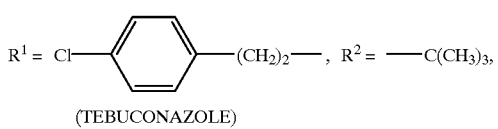

(II-1)

$R^1 = $ Cl—⟨benzene⟩—$(CH_2)_2$—, $R^2 = $ —$C(CH_3)_3$, (TEBUCONAZOLE)

$R^3 = OH$, $n = 1$, (II-2)

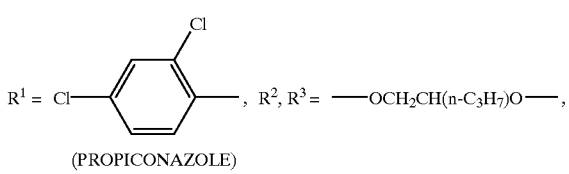

(PROPICONAZOLE)

$n = 1$, (II-3)

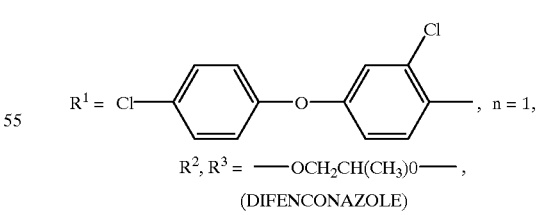

$R^2, R^3 = $ —$OCH_2CH(CH_3)O$—, (DIFENCONAZOLE)

(II-4)

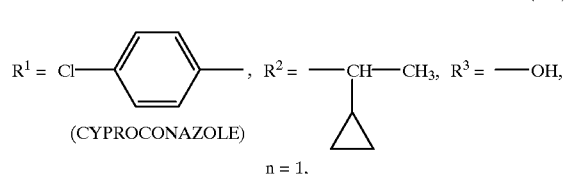

(CYPROCONAZOLE)

$n = 1$,

-continued (II-5)
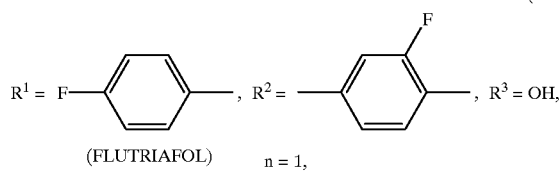
(FLUTRIAFOL)
$R^1 = F$-phenyl, $R^2 =$ 3-fluorophenyl, $R^3 = OH$, n = 1, (II-6)
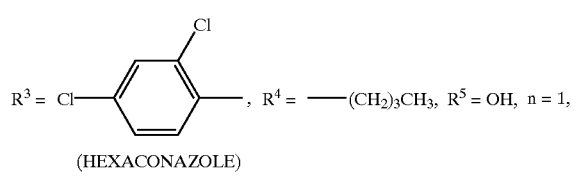
(HEXACONAZOLE)
$R^3 =$ 2,4-dichlorophenyl, $R^4 = -(CH_2)_3CH_3$, $R^5 = OH$, n = 1, (II-7)
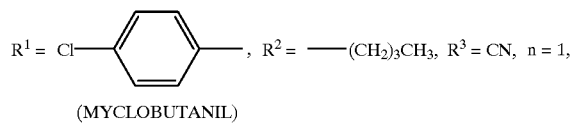
(MYCLOBUTANIL)
$R^1 =$ 4-Cl-phenyl, $R^2 = -(CH_2)_3CH_3$, $R^3 = CN$, n = 1, (II-8)
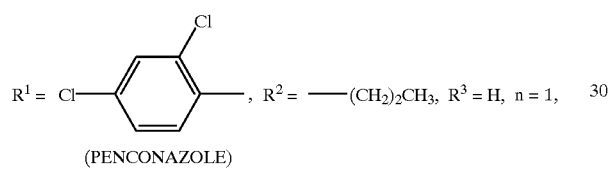
(PENCONAZOLE)
$R^1 =$ 2,4-dichlorophenyl, $R^2 = -(CH_2)_2CH_3$, $R^3 = H$, n = 1, (II-9)
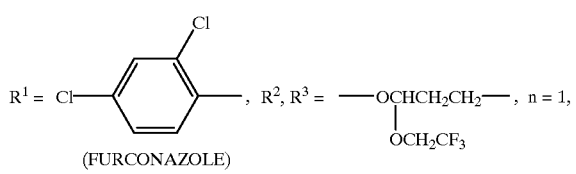
(FURCONAZOLE)
$R^1 =$ 2,4-dichlorophenyl, $R^2, R^3 = -OCHCH_2CH_2-$ / $OCH_2CF_3$, n = 1, (II-10)
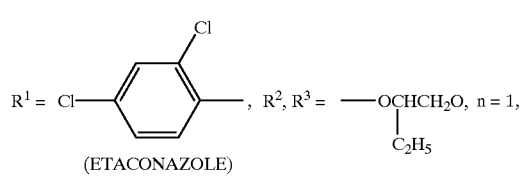
(ETACONAZOLE)
$R^1 =$ 2,4-dichlorophenyl, $R^2, R^3 = -OCHCH_2O-$ / $C_2H_5$, n = 1, (II-11)
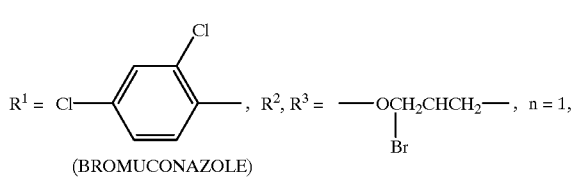
(BROMUCONAZOLE)
$R^1 =$ 2,4-dichlorophenyl, $R^2, R^3 = -OCH_2CHCH_2-$ / Br, n = 1, (II-12)
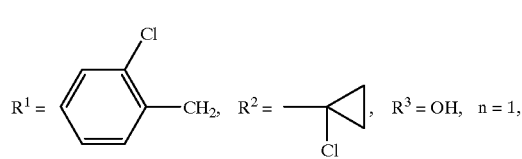
$R^1 =$ 2-chlorobenzyl-$CH_2$, $R^2 =$ chlorocyclopropyl, $R^3 = OH$, n = 1, (II-13)
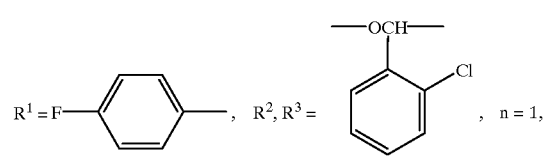
$R^1 =$ 4-F-phenyl, $R^2, R^3 =$ (2-chlorophenyl)(OCH_3)CH-, n = 1, (II-14)
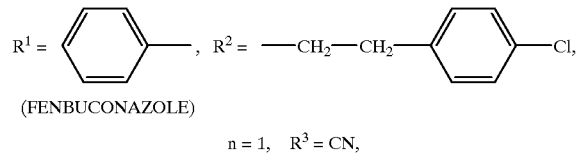
(FENBUCONAZOLE)
$R^1 =$ phenyl, $R^2 = -CH_2-CH_2-$(4-Cl-phenyl),
n = 1, $R^3 = CN$, (II-15)
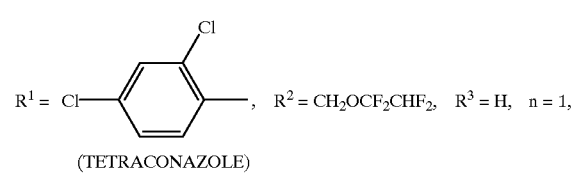
(TETRACONAZOLE)
$R^1 =$ 2,4-dichlorophenyl, $R^2 = CH_2OCF_2CHF_2$, $R^3 = H$, n = 1, (II-16)
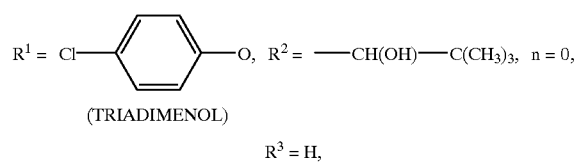
(TRIADIMENOL)
$R^1 =$ 4-Cl-phenyl-O, $R^2 = -CH(OH)-C(CH_3)_3$, n = 0, $R^3 = H$, (II-17)
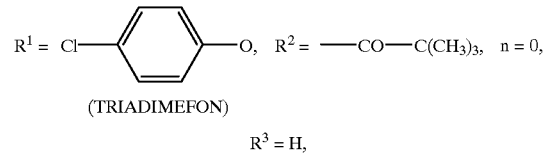
(TRIADIMEFON)
$R^1 =$ 4-Cl-phenyl-O, $R^2 = -CO-C(CH_3)_3$, n = 0, $R^3 = H$, (II-18)
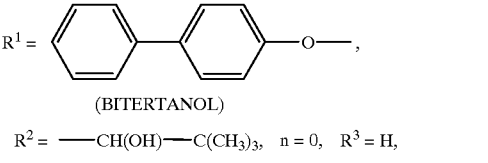
(BITERTANOL)
$R^1 =$ biphenyl-O-,
$R^2 = -CH(OH)-C(CH_3)_3$, n = 0, $R^3 = H$, (II-19)
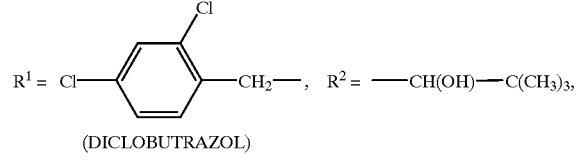
(DICLOBUTRAZOL)
$R^1 =$ 2,4-dichlorobenzyl-$CH_2-$, $R^2 = -CH(OH)-C(CH_3)_3$,
n = 0, $R^3 = H$, (II-20)
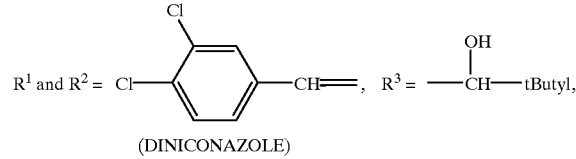
(DINICONAZOLE)
$R^1$ and $R^2 =$ 3,4-dichlorophenyl-CH=, $R^3 = -CH(OH)-$tButyl, (2) Azole derivatives of the formula (III)

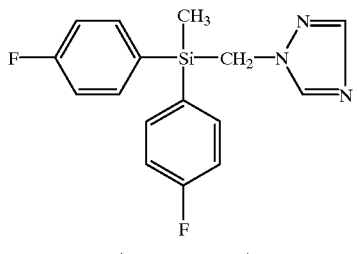

(FLUSILAZOLE)

(3) The azole derivative of the formula (IV)

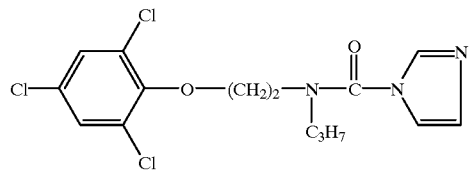

(PROCHLORAZ)

(4) The compound (V)

$$S_x$$

(5) Azole derivative of the formula (VI)

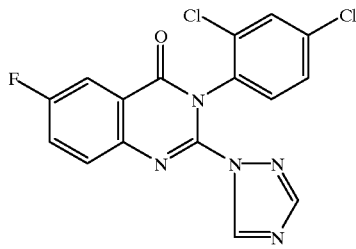

(FLUQUINCONAZOLE)

(6) Heterocycles of the formula (VII)

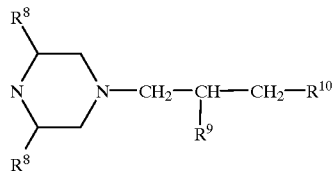

$X = 0, \quad R^8 = CH_3, \quad R^9 = H, \quad R^{10} = C_{10}H_{21}$ (VII-1)

(TRIDEMORPH)

$X = 0, \quad R^8 = CH_3, \quad R^9 = H, \quad R^{10} = C_9H_{19},$ (VII-2)

(ALDIMORPH)

$X = 0, \quad R^8 = CH_3, \quad R^9 = CH_3, \quad R^{10} =$ 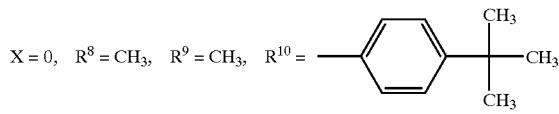 (VII-3)

(FENPROPIMORPH)

$X = CH_2, \quad R^8 = H, \quad R^9 = CH_3, \quad R^{10} =$ 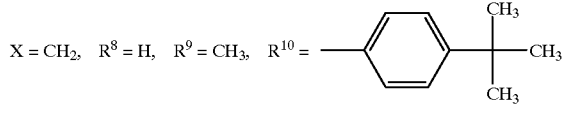 (VII-4)

(FENPROPIDIN)

(7) Compound of the formula (VIII)

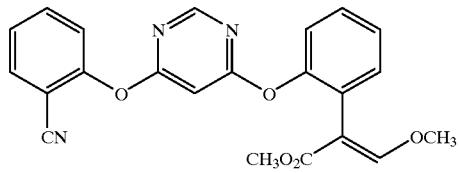

(8) Compound of the formula (IX)

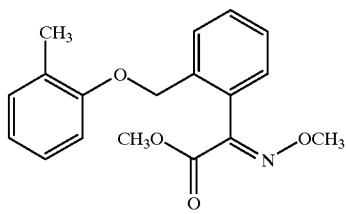

(9) Compound of the formula (X)

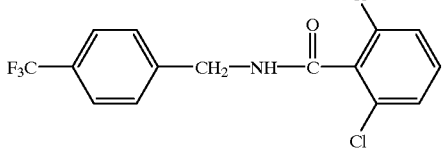

(10) Compound of the formula (XI)

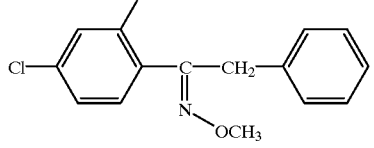

(PYRIFENOX)

(11) Compound of the formula (XII)

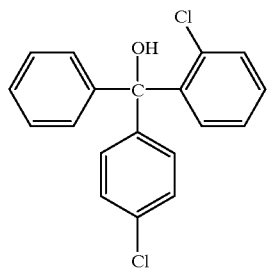

(FENARIMOL)

(12) Compound of the formula (XIII)

(TRIFLUMIZOLE)

(13) Compound of the formula (XIV)

$R^{11}$ =

(VINCLOZOLIN) (XIV-1)

$R^{11}$ =

(PROCYMIDONE) (XIV-2)

$R^{11}$ =  —CO—NH—CH(CH$_3$)$_2$ (IPRODIONE) (XIV-3)

(14) Compounds of the formula (XV)

$R^{12}$ = CH$_3$
(PYRIMETHANIL) (XV-1)

$R^{12}$ = C≡C—CH$_3$
(MEPANIPYRIM) (XV-2)

(15) Compounds of the formula (CH$_3$)$_2$N—SO$_2$—N—S—CCl$_2$F (XVI)

$R^{13}$ = H
(DICHLORFLUANID) (XVI-1)

$R^{13}$ = CH$_3$
(TOLYLFLUANID) (XVI-2)

(16) Compound of the formula (XVII)

(DITHIANON)

(17) Compound of the formula (XVIII)

H$_3$C—(CH$_2$)$_{11}$—NH—C(=NH)—NH$_2$ · CH$_3$CO$_2$H (DODINE)

(18) Compound of the formula (XIX)

(CHLOROTHALONIL)

(19) Compound of the formula (XX)

(DIMETHOMORPH)

(20) Compound of the formula (XXI)

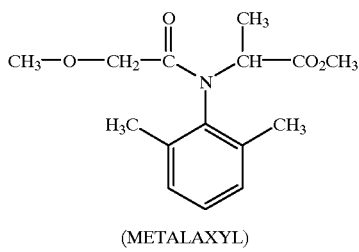

(METALAXYL)

(21) Compound of the formula (XXII)

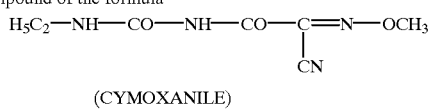

(CYMOXANILE)

(22) Compound of the formula (XXIII)

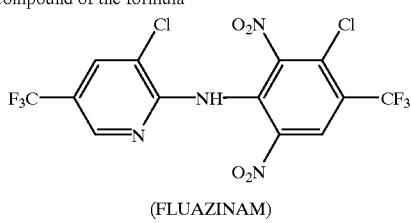

(FLUAZINAM)

(23) Compound of the formula (XXIV)

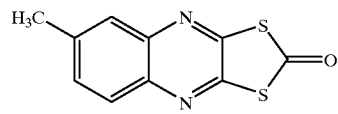

(24) Compounds of the formula (XXV)

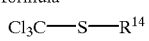

(XXV-1)

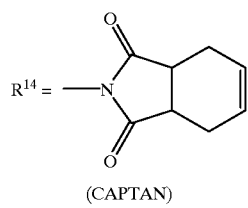

(CAPTAN)

(XXV-2)

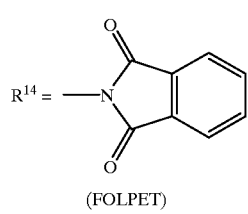

(FOLPET)

(25) Compound of the formula (XXVI)

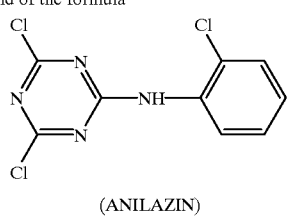

(ANILAZIN)

(26) Compound of the formula (XXVII)

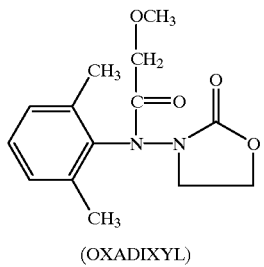

(OXADIXYL)

(27) Compound of the formula (XXVIII)

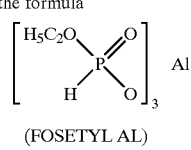

(FOSETYL AL)

(28) Compound of the formula (XXIX)

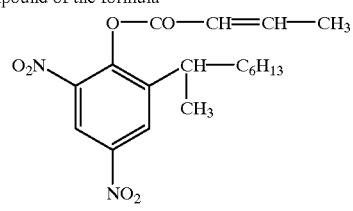

(DINOCAP)

(29) Compound of the formula (XXX)

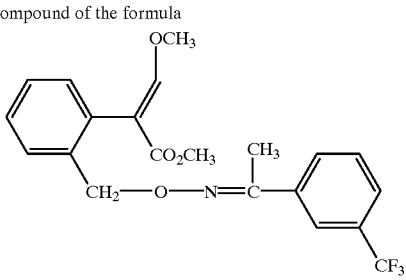

(30) Compound of the formula (XXXI)

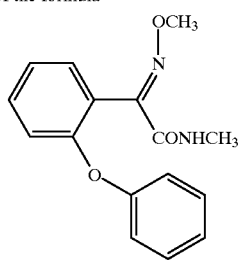

(31) Compound of the formula

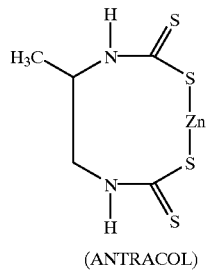

(ANTRACOL)

(32) Compounds of the formula

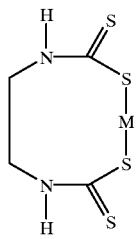

M = Zn
(ZINEB)

M = Mn
(MANEB)

M = Mn/Zn
(Mancozeb)

(33) Compound of the formula

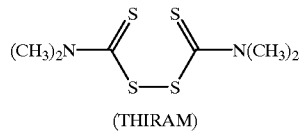

(THIRAM)

(34) Compound of the formula

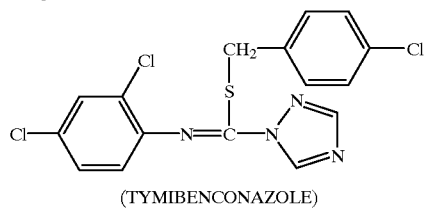

(TYMIBENCONAZOLE)

(35) Compound of the formula

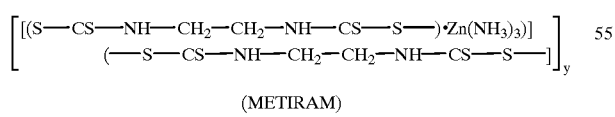

(METIRAM)

(36) Compound of the formula

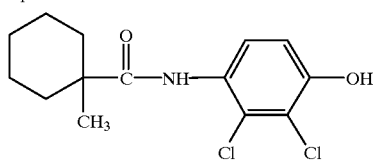

(37) Compound of the formula

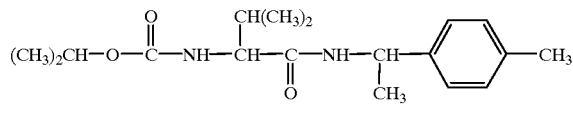

(38) Compounds of the formula

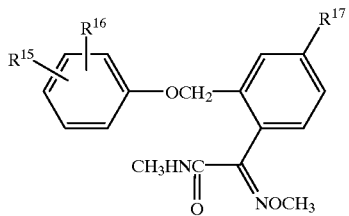

in which
$R^{15}$ and $R^{16}$, independently of each other, represent hydrogen, halogen, methyl or phenyl, and
$R^{17}$ represents hydrogen or methyl,

(39) 8-$^t$Butyl-2-(N-ethyl-N-n-propylamino)-methyl-1,4-dioxaspiro[4.5]decane of the formula

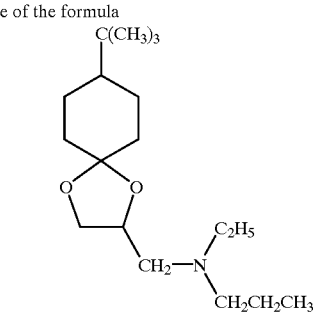

(40) Compound of the formula

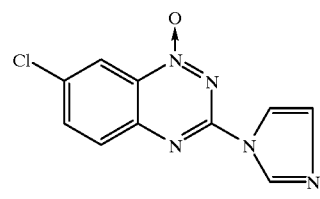

(41) Compound of the formula

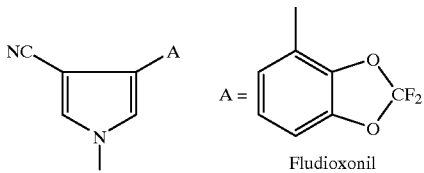

(42) Compound of the formula

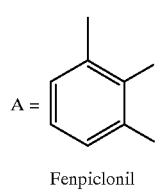 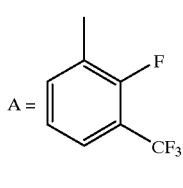

Fenpiclonil

(43) Compound of the formula

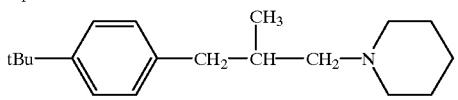

(44) Benzimidazole of the formula

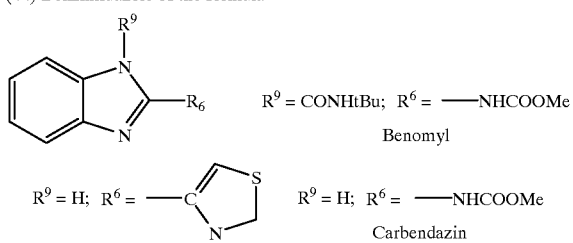

(45) Compound of the formula

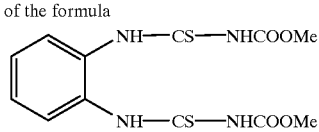

(46) Compound of the formula

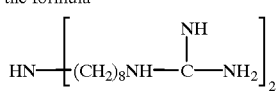

(47) Compound of the formula

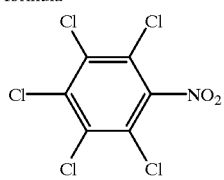

The active compounds of the formula (I) are known for example from EP-OS (European Published Specification) 192 060.

The fungicidal active compounds are also known.

In the following publications, for example, there are described:

(1) Compounds of the formula (II)
DE-OS (German Published Specification) 2 201 063
DE-OS (German Published Specification) 2 324 010
DE-OS (German Published Specification) 2 737 489
DE-OS (German Published Specification) 3 018 866
DE-OS (German Published Specification) 2 551 560
EP 47 594
DE 2 735 872

(2) Compound of the formula (III)
EP 68 813
U.S. Pat. No. 4,496,551

(3) Compound of the formula (IV)
DE-OS (German Published Specification) 2 429 523
DE-OS (German Published Specification) 2 856 974
U.S. Pat. No. 4,108,411

(6) Compounds of the formula (VII)
DL 140 041

(7) Compound of the formula (VIII)
EP 382 375

(8) Compound of the formula (IX)
EP 515 901

(9) Compound of the formula (X)
EP 314 422

(10) Compound of the formula (XI)
EP 49 854

(11) Compound of the formula (XII)
DE-OS (German Published Specification) 1 770 288
U.S. Pat. No. 3 869 456

(13) Compounds of the formula (XIV)
DE 2 207 576
U.S. Pat. No. 3,903,090
U.S. Pat. No. 3,755,350
U.S. Pat. No. 3,823,240

(14) Compounds of the formula (XV)
EP 270 111

(19) Compound of the formula (XX)
EP 219 756

(34) Compound of the formula (XXXV)
U.S. Pat. No. 4,512,989

(38) Compounds of the formula (XXXIX)
EP 398 692

Compounds of groups (15), (16), (17), (18), (23), (34), (25), (28), (31), (32), (33) and (38) to (47) are described for example in K. H. Büchel, "Pflanzenschutz und Sch ädlingsbekämpfung [Crop protection and pest control]", pages 121–153, Georg Thieme-Verlag, Stuttgart, 1977. The compound of group (39) is known from EP-OS (European Published Specification) 281 842.

Besides the active compound of the formula (I), the active compound combinations according to the invention contain at least one fungicidal active compound, selected for example from the compounds of groups (1) to (47). Additionally, they may also contain other active compounds and also customary auxiliaries and additives and diluents.

A synergistic effect is particularly apparent when the active compounds in the active compound combinations according to the invention are present in particular weight ratios. However, the weight ratios of the active compounds in the active compound combinations can be varied within a relatively wide range. In general 0.1 to 10 parts by weight, preferably 0.3 to 3 parts by weight, of at least one fungicidal active compound from the groups (1) to (48) is/are allocated to one part by weight of active compound of the formula (I).

The combinations of active compounds according to the invention possess very good fungicidal properties. They can be employed, in particular, for controlling phytopathogenic fungi, such as Plasmodiophoromycetes, Oomycetes, Chytridiomycetes, Zygomycetes, Ascomycetes, Basidiomycetes, Deuteromycetes etc.

The active compound combinations according to the invention are particularly suitable for controlling cereal diseases, such as Erysiphe, Cochliobolus, Septoria, Pyrenophora and Leptosphaeria, and for use against fungal infestations of vegetables, grapes and fruit, for example against Venturia or Podosphaera on apples, Uncinula on vine plants or Sphaeroteca on cucumbers.

The active compound combinations are also suitable for controlling animal pests, preferably anthropods, in particular insects encountered in agriculture, in forestry, in the protection of stored products and of materials, and in the hygiene field. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and Scutigera spec.

From the order of the Symphyla, for example, *Scutigerella immaculata*.

From the order of the Thysanura, for example, *Lepisma saccharina*.

From the order of the Collembola, for example, *Onychiurus armatus*.

From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria*.

From the order of the Dermaptera, for example, *Forficula auricularia*.

From the order of the Isoptera, for example, Reticulitermes spp.

From the order of the Anoplura, for example, *Pediculus humanus corporis,* Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci*.

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi, Phylloxera vastrix,* Pemphigus spp., Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp. *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana*.

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica*.

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa*.

The fact that the active compound combinations are well tolerated by plants at the concentrations required for controlling plant diseases permits a treatment of aerial parts of plants, of propagation stock and seeds, and of the soil.

The active compounds of the invention can be converted to the customary formulations, such as solutions, emulsions, suspensions, powders, foams, pastes, granules, aerosols, very fine capsules in polymeric substances and in coating compositions for seed, as well as ULV formulations.

These formulations are produced in a known manner, for example by mixing the active compounds with extenders, that is, liquid solvents, liquefied gases under pressure, and/or solid carriers, optionally with the use of surface-active agents, that is emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compound combinations according to the invention can be present in the formulations as mixtures with other known active compounds, such as fungicides, insecticides, acaricides and herbicides, and also as mixtures with fertilizers or plant growth regulators.

The active compound combinations can be used as such, in the form of their formulations or as the use forms prepared therefrom, such as ready-to-use solutions, emulsifiable concentrates, emulsions, suspensions, wettable powders, soluble powders and granules.

They are used in the customary manner, for example by watering, spraying, atomizing, scattering, brushing on and as a powder for dry seed treatment, a solution for seed treatment, a water-soluble powder for seed treatment, a water-soluble powder for slurry treatment, or by encrusting.

In the treatment of parts of plants, the concentrations of active compound in the use forms can be varied within a substantial range. In general, they are between 1 and 0.0001% by weight, preferably between 0.5 and 0.001%.

In the treatment of seed, amounts of 0.001 to 50 g of active compound per kilogram of seed are generally required, preferably 0.01 to 10 g.

In the treatment of the soil, active compound concentrations from 0.00001 to 0.1% by weight, preferably 0.0001 to 0.02% by weight, are required at the site of action.

The good fungicidal activity of the active compound combinations according to the invention can be seen from the examples which follow. While the individual active compounds or the known active compound combinations show weaknesses with regard to the fungicidal activity, the tables of the examples which follow show clearly that the activity found in the case of the active compound combinations according to the invention exceeds the total of the activities of individual active compounds and also exceeds the activities of the known active compound combinations.

In the examples that follow, imidacloprid is employed as active compound of the formula (I). The fungicidal active compounds also used are stated in the examples.

EXAMPLE A

*Drechslera graminea* test (barley)/seed treatment (syn. *Helminthosporium gramineum*)

The active compounds are used as a powder for dry seed treatment. They are prepared by extending the active compound in question with rock meal to give a finely pulverulent mixture which ensures uniform distribution on the seed surface.

To carry out the seed treatment, the infected seed and the seed-dressing product are shaken for 3 minutes in a sealed glass flask.

The seed, embedded in screened, moist standard soil in sealed Petri dishes, is exposed to a temperature of 4° C. for 10 days in a refrigerator. This triggers germination of the barley and, if appropriate, of the fungal spores. 2×50 pregerminated barley kernels are subsequently sown in standard soil at a depth of 3 cm and grown in a greenhouse at a temperature of approximately 18° C. in seed boxes which are exposed to the light for 15 hours per day.

Approximately 3 weeks after sowing, the plants are evaluated for symptoms of barley leaf stripe.

Mixtures of imidacloprid with tebuconazole, captan, euparen M, bitertanol, triazoxide, thiram, fludioxonil exhibit a pronounced increase in activity as compared with treatment using the individual compounds.

EXAMPLE B

*Fusarium nivale* Test (wheat)/seed Treatment

The active compounds are used as a powder for dry seed treatment. They are prepared by extending the active compound in question with rock meal to give a finely pulverulent mixture which ensures uniform distribution on the seed surface.

To carry out the seed treatment, the infected seed and the seed-dressing product are shaken for 3 minutes in a sealed glass flask.

2×100 wheat kernels are subsequently sown in standard soil at a depth of 1 cm and grown in the greenhouse at a temperature of approximately 10° and a relative atmospheric humidity of approximately 95% in seed boxes which are exposed to the light for 15 hours per day.

Approximately 3 weeks after sowing, the plants are evaluated for snow blight symptoms.

Mixtures of imidacloprid with euparen, guazatine, triadimenol, difenconazole, fenpiclonil exhibit a pronounced increase in activity as compared with treatment using the individual compounds.

EXAMPLE C

*Phaedon larvae* Test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of the active compound of the desired concentration and are infested with mustard beetle larvae (*Phaedon cochleariae*), as long as the leaves are still moist.

After 7 days the destruction in % is determined.

Mixtures of imidacloprid with anilazine, benomyl, bitertanol, captan, diclofluanid, mancozeb, maneb, metalaxyl, prochloraz, procymidone, sulphate, tolylfluanid, triadimefon, triadimenol exhibit a pronounced increase in activity as compared with treatment using the individual compounds.

EXAMPLE D

Myzus Test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) heavily infested with aphids (*Myzus persicae*) are treated by dipping in the preparation of active compound of the desired concentration.

After 6 days, the destruction in % is determined.

Mixtures of imidacloprid with bitertanol, fenpropimorph, prochloraz, tebuconazole exhibit a pronounced increase in activity as compared with treatment using the individual compounds.

EXAMPLE E

Botrytis Test (beans)/protective

Solvent: 4.7 parts by weight of acetone

Emulsifier: 0.3 parts by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

To test for protective activity, young plants are sprayed with the preparation of active compound until dripping wet. After the spray coating has dried on, two small pieces of agar covered with *Botrytis cinerea* are placed on each leaf. The inoculated plants are placed in a darkened humid chamber at 20° C. 3 days after the inoculation, the size of the infected spots on the leaves is evaluated.

Mixtures of imidacloprid with procymidone, tolyfluanid, tebuconazole exhibit a pronounced increase in activity as compared with treatment using the individual compounds.

EXAMPLE F

Podosphaera Test (apple)/protective

Solvent: 4.7 parts by weight of acetone

Emulsifier: 0.3 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated by dusting with conidia of the causative organism of apple mildew (*Podosphaera leucotricha*).

The plants are then placed in a greenhouse at 23° C. and a relative atmospheric humidity of about 70%.

Evaluation is carried out 10 days after the inoculation.

Mixtures of imidacloprid with fenpropidin, triadimenol exhibit a prounced increase in activity as compared with treatment using the individual compounds.

What is claimed is:

1. A composition comprising synergistic amounts of:

imidaclopird; and the compound of formular XXXVIII

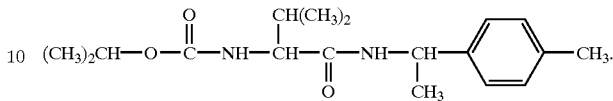

2. The composition of claim 1, wherein the composition comprises 0.1 to 10 parts by weight of compound XXXVIII per part by weight of imidacloprid.

3. The composition of claim 1, comprising 0.3 to 3 parts by weight of compound XXXVIII per part by weight of imidacloprid.

4. A process for preparing composition of claim 1, comprises mixing imidacloprid and compound XXXVIII with at least one ingredient selected from extenders, surface-active substances and mixtures thereof.

5. A process for the control of at least one fungi and insects, comprising applying the composition of claim 1 to at least one of fungi, insects, fungi habitat, and insect habitat; wherein the composition is applied at a concentration sufficient for controlling plant disease.

6. The process of claim 5, wherein the step of applying comprises treating seed with from 0.001 to 50 g of compound XXXVIII per kilogram of seed.

7. The process of claim 5, wherein the step of applying comprises treating soil with from 0.00001 to 0.1% by weight, compound XXXVIII.

8. The process of claim 5, wherein the weight ratio of imidacloprid to compound XXXVIII is from 1:0.1 to 1:10 and the composition is applied at a concentration sufficient for controlling plant disease.

* * * * *